(12) United States Patent
Bar et al.

(10) Patent No.: US 11,587,228 B2
(45) Date of Patent: Feb. 21, 2023

(54) CROSS MODALITY TRAINING OF MACHINE LEARNING MODELS

(71) Applicant: Nano-X AI Ltd., Shefayim (IL)

(72) Inventors: Amir Bar, Berkeley, CA (US); Raouf Muhamedrahimov, San Francisco, CA (US); Rachel Wities, Givat Shmuel (IL)

(73) Assignee: Nano-X AI Ltd., Shefayim (IL)

( * ) Notice: Subject to any disclaimer, the term of this patent is extended or adjusted under 35 U.S.C. 154(b) by 238 days.

(21) Appl. No.: 16/989,968

(22) Filed: Aug. 11, 2020

(65) Prior Publication Data

US 2022/0051396 A1  Feb. 17, 2022

(51) Int. Cl.
| | |
|---|---|
| G06K 9/00 | (2022.01) |
| G06T 7/00 | (2017.01) |
| G06F 40/20 | (2020.01) |
| G16H 30/40 | (2018.01) |

(Continued)

(52) U.S. Cl.
CPC ............ G06T 7/0012 (2013.01); G06F 40/20 (2020.01); G06N 20/00 (2019.01); G16H 15/00 (2018.01); G16H 30/40 (2018.01); G06T 2207/20081 (2013.01); G06T 2207/20084 (2013.01); G06T 2207/30016 (2013.01)

(58) Field of Classification Search
CPC ......... G06T 7/0012; G06T 2207/20081; G06T 2207/20084; G06T 2207/10081; G06T 2207/10088; G06T 2207/10132; G06T 2207/10116; G06T 2207/20076; G06T 2207/30004; G06T 2200/24; G06T 2207/30061; G06T 7/0014; G06T 7/11; G06T 2207/10072; G06T 2207/30008; G06T 7/187; G06T 2207/10048; G06T 2207/30016; G06T 5/008; G06T 7/70; G06T 11/001; G16H 50/20; G16H 30/40; G16H 15/00; G16H 50/70; G16H 10/60; G16H 30/20; G16H 50/30; G16H 40/20
See application file for complete search history.

(56) References Cited

U.S. PATENT DOCUMENTS

| | | | |
|---|---|---|---|
| 2011/0106740 A1 * | 5/2011 | Yeatman ................ | G16H 50/20 706/20 |
| 2019/0340753 A1 * | 11/2019 | Brestel ................... | G16H 15/00 |

OTHER PUBLICATIONS

Zhang, TandemNet: Distilling Knowledge from Medical Images Using Diagnostic Reports as Optional Semantic References, arXiv (Year: 2017).*

* cited by examiner

*Primary Examiner* — Alex Kok S Liew

(57) ABSTRACT

There is provided a method, comprising: providing a training dataset including, medical images and corresponding text based reports, and concurrently training a natural language processing (NLP) machine learning (ML) model for generating a NLP category for a target text based report and a visual ML model for generating a visual finding for a target image, by: training the NLP ML model using the text based reports of the training dataset and a ground truth comprising the visual finding generated by the visual ML model in response to an input of the images corresponding to the text based reports of the training dataset, and training the visual ML model using the images of the training dataset and a ground truth comprising the NLP category generated by the NLP ML model in response to an input of the text based reports corresponding to the images of the training dataset.

17 Claims, 5 Drawing Sheets

(51) Int. Cl.
*G06N 20/00* (2019.01)
*G16H 15/00* (2018.01)

CROSS MODALITY TRAINING OF MACHINE LEARNING MODELS

FIELD AND BACKGROUND OF THE INVENTION

The present invention, in some embodiments thereof, relates to machine learning (ML) models and, more specifically, but not exclusively, to training an ML model using a training dataset with no labels or minimal labels.

Labelling data for training a ML models affects performance of the ML model. However, standard labelling processes are manual, which are slow, expensive and prone to error at best, or at worst, not available. Manual labeling of medical images is performed by a trained professional that looks at the image, and assigns a ground truth label of whether a certain visual finding is present in the image or not, for example, whether a CT image slice of a brain depicts bleeding in the brain or not.

SUMMARY OF THE INVENTION

According to a first aspect, a computer implemented method for training a visual machine learning (ML) model component and a natural language processing (NLP) ML model component, comprises: providing a training dataset including, for each of a plurality of sample individuals, a medical image and a corresponding text based report, providing the NLP ML model component for generating an outcome of at least one NLP category in response to an input of a target text based report, providing the visual ML model component for generating an outcome of at least one visual finding in response to an input of a target image, and concurrently training the NLP ML model component and the visual ML model component using the training dataset, by: training the NLP ML model using an input of the text based reports of the training dataset and a ground truth comprising the outcome of the at least one visual finding generated by the visual ML model in response to an input of the images corresponding to the text based reports of the training dataset, training the visual ML model using an input of the images of the training dataset and a ground truth comprising the outcome of the at least one NLP category generated by the NLP ML model in response to an input of the text based reports corresponding to the images of the training dataset.

According to a second aspect, a computer implemented method for identification of at least one visual finding in a medical image, comprises: receiving a medical image of a subject, inputting the medical image into a visual ML model, and obtaining an outcome of the visual ML model, indicative of at least one visual finding of the medical image, wherein the visual ML model comprises a visual ML model component that is concurrently trained with an NLP ML model component on a training dataset including, for each of a plurality of sample individuals, a medical image and a corresponding text based report, wherein the NLP ML model component generates an outcome of at least one NLP category in response to an input of a target text based report, wherein the visual ML model component generates an outcome of at least one visual finding in response to an input of a target image, and wherein the concurrently training is performed by: training the NLP ML model using an input of the text based reports of the training dataset and a ground truth comprising the outcome of the at least one visual finding generated by the visual ML model in response to an input of the images corresponding to the text based reports of the training dataset, and training the visual ML model using an input of the images of the training dataset and a ground truth comprising the outcome of the at least one NLP category generated by the NLP ML model in response to an input of the text based reports corresponding to the images of the training dataset.

According to a third aspect, a computer implemented method for identification of at least one NLP category in a text based report of a medical image, comprising: receiving a text based report of a medical image of a subject, inputting the text based report into a NLP ML model, and obtaining as an outcome of the NLP ML model, at least one NLP category indicative of at least one visual finding of the medical image described in the text based report, wherein the NLP ML model comprises a NLP ML model component that is concurrently trained with a visual ML model component on a training dataset including, for each of a plurality of sample individuals, a medical image and a corresponding text based report, wherein the NLP ML model component generates an outcome of at least one NLP category in response to an input of a target text based report, wherein the visual ML model component for generates an outcome of at least one visual finding in response to an input of a target image, and wherein the concurrently training is performed by: training the NLP ML model using an input of the text based reports of the training dataset and a ground truth comprising the outcome of the at least one visual finding generated by the visual ML model in response to an input of the images corresponding to the text based reports of the training dataset, and training the visual ML model using an input of the images of the training dataset and a ground truth comprising the outcome of the at least one NLP category generated by the NLP ML model in response to an input of the text based reports corresponding to the images of the training dataset.

In a further implementation form of the first, second, and third aspects, the NLP ML model is trained using a supervised approach with the input of the based reports and the ground truth outcome of the visual ML model, and concurrently the visual ML model is trained using a supervised approach with the input of the images and the ground truth outcome of the NLP ML model.

In a further implementation form of the first, second, and third aspects, the concurrently training is performed iteratively.

In a further implementation form of the first, second, and third aspects, further comprising: prior to the concurrently training, weakly labelling a subset of the text based reports of the training dataset with a weak label indicative of presence or absence of the at least one NLP category in respective target based reports, and wherein the concurrently training is performed using the training dataset with weak labels of the text based reports.

In a further implementation form of the first, second, and third aspects, weakly labelling comprises weakly labelling about 5-20% of the text based reports of the training dataset with the weak label.

In a further implementation form of the first, second, and third aspects, weakly labelling comprises automatically weakly labelling the subset of the text based reports using a simple set of rules.

In a further implementation form of the first, second, and third aspects, the at least one NLP category outcome of the NLP ML model and the at least one visual finding outcome of the visual ML model are from a common set and of a same format.

In a further implementation form of the first, second, and third aspects, each of the at least one NLP category outcome of the NLP ML model and the at least one visual finding outcome of the visual ML model is a binary classification indicative of positive or negative finding found in the image and corresponding text based report.

In a further implementation form of the first, second, and third aspects, the at least one NLP category outcome of the NLP ML model component is an indication of a visual finding depicted in an image corresponding to a text based report inputted into the NLP ML model component, and the at least one visual finding outcome of the visual ML model component is an indication of the visual finding depicted in the image corresponding to the text based report inputted into the NLP ML model component.

In a further implementation form of the first, second, and third aspects, further comprising: computing a correlation value indicative of a correlation between the at least one NLP category outcome of the NLP ML model and the at least one visual finding outcome of the visual ML model for an input of an image and corresponding text based report, and in response to the correlation value being below a threshold indicative of dis-correlation between the at least one NLP category outcome of the NLP ML model and the at least one visual finding outcome of the visual ML model, storing the image and corresponding text based report in a user-training dataset, and providing the user-training dataset for presentation on a display.

In a further implementation form of the first, second, and third aspects, concurrently training comprises concurrently training the NLP ML model component and the visual ML model component using a combined visual and NLP consensus loss function.

In a further implementation form of the first, second, and third aspects, the combined visual and NLP consensus loss function comprises a cross model consensus loss function that encourages high consensus between the NLP ML model and the visual ML model.

In a further implementation form of the first, second, and third aspects, concurrently training further comprises training the NLP ML model component using an NLP loss function that is computed for the training of the NLP ML model and excludes data obtained from the training of the visual ML model component.

In a further implementation form of the first, second, and third aspects, the NLP ML model comprises a binary classifier and the NLP loss function comprises a standard binary cross entropy loss.

In a further implementation form of the first, second, and third aspects, the NLP loss function penalizes the NLP ML model for errors made during an initial inaccurate labeling of a subset of text based reports of the training dataset made prior to the concurrently training.

In a further implementation form of the first, second, and third aspects, the visual ML model component is implemented as a neural network.

In a further implementation form of the first, second, and third aspects, the NLP ML model component is implemented as a neural network.

In a further implementation form of the first, second, and third aspects, a target text report is inputted into an NLP processing path comprising the NLP ML model component that generates the NLP category, and a target image corresponding to the target text report is inputted in a visual processing path comprising the visual ML model component that generates the at least one visual finding, wherein the NLP processing path and the visual processing path are concurrently executed during the concurrent training.

In a further implementation form of the second aspect, further comprising: receiving a receiving a text based report corresponding to the medical image of the subject inputted into the visual ML model, inputting the text based report into a NLP ML model, obtaining as an outcome of the NLP ML model, at least one NLP category indicative of at least one visual finding of the medical image described in the text based report, wherein the NLP ML model comprises the NLP ML model component that is concurrently trained with the visual ML model component on the training dataset, and generating an alert when the at least one NLP category outcome of the NLP ML model does not match the at least one visual finding outcome of the visual ML model.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
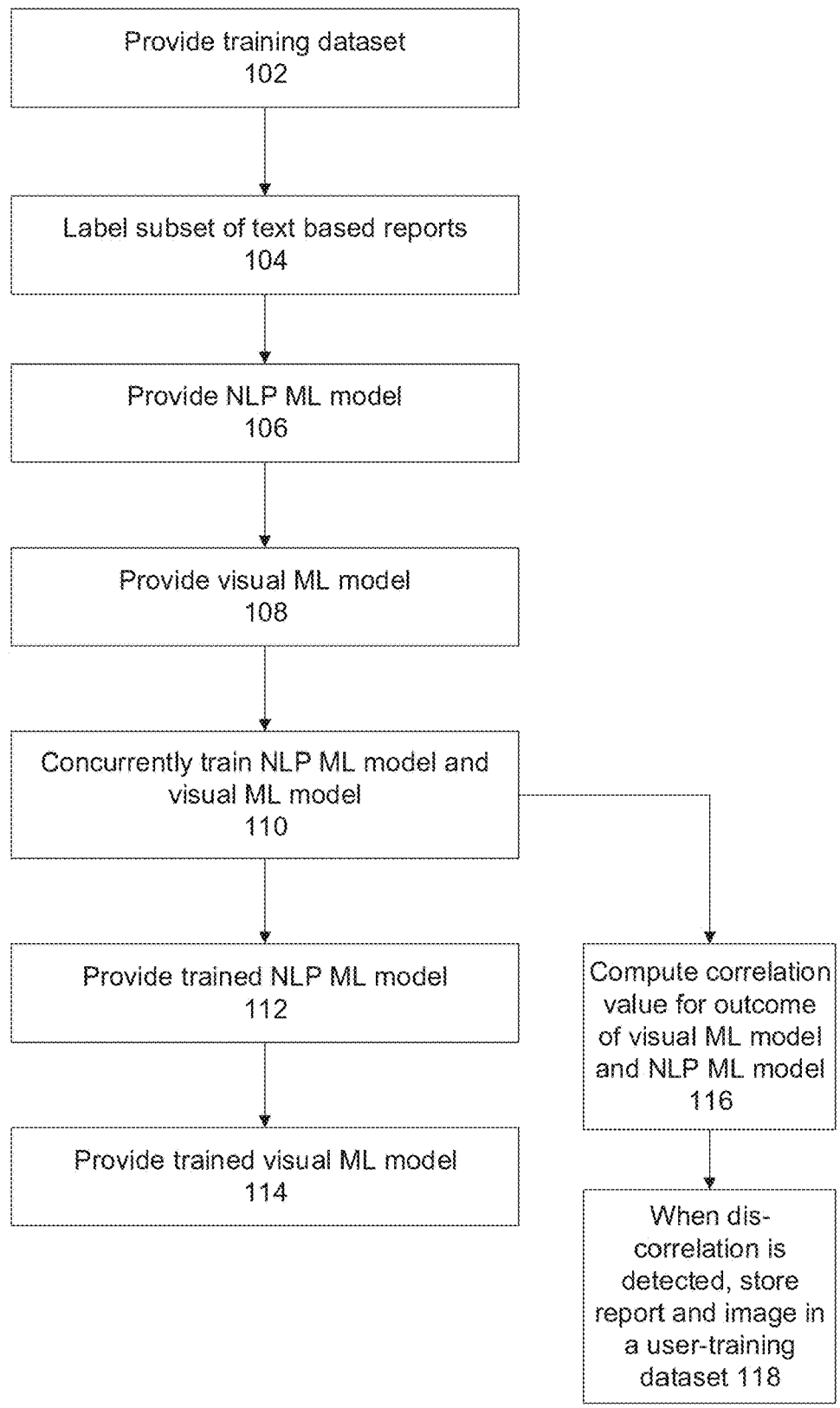
FIG. 1 is a flowchart of a method for concurrent training of a visual machine learning (ML) model component and a natural language processing (NLP) ML model component, in accordance with some embodiments of the present invention.

The present invention, in some embodiments thereof, relates to machine learning (ML) models and, more specifically, but not exclusively, to training an ML model using a training dataset with no labels or minimal labels.

An aspect of some embodiments of the present invention relates to systems, methods, an apparatus, and/or code instructions (i.e., stored on a memory and executable by hardware processor(s)) for concurrently training a visual machine learning (ML) model component and a natural language processing (NLP) ML model component on a training dataset of medical images and corresponding text based reports (describing the medical images) of multiple subjects, for example, CT scans and corresponding radiology reports. Each image, which is designed to be fed into the visual ML model, is associated with a corresponding text based report, which is designed to be fed into the NLP ML model. The concurrent training is performed by using a supervisory approach, where the outcome of one ML model is used to provide a ground truth for the other ML model, simultaneously. The concurrent training increase the accuracy of the trained NLP ML model and/or the trained visual ML model, in comparison to training each ML model independently using the respective component of the training dataset.

The outcome of the NLP ML model (in response to an input of text based reports for which the corresponding images are inputted into the visual ML model) is used to supervise the training of the visual ML model (which receives the image as input, where the images correspond to the text based reports inputted into the NLP ML model to generate the outcome), while concurrently, the outcome of the visual ML model (in response to an input of the images for which the corresponding text based reports are inputted into the NLP ML model) is used to supervise the training of the NLP ML model (which receives the text reports as input, where the text reports correspond to the images inputted into the visual ML model to generate the respective outcome).

Optionally, prior to the concurrent training, a small subset of the text based reports are weakly labelled, optionally inaccurately, by manual and/or automated processes. The initial weak labeling may serve as an initial seed for the iterative concurrent training. During the iterative concurrent training, errors in the initial weak labelling may be automatically corrected. The training of the NLP and/or visual ML models is performed using the initial weak, optionally inaccurate, labelling of the subset, rather than requiring labeling of the complete training dataset as in standard supervised approaches.

Optionally, the concurrent training is performed using a combined visual and NLP consensus loss function that is used for the training of each of the NLP ML model and the visual ML model.

At least some implementations of the systems, methods, apparatus, and/or code instructions described herein address the technical problem of training a visual ML model for identifying visual features in un-labelled medical images and/or of training a NLP ML model for identifying NLP categories in un-labelled text based reports of medical images (e.g., radiology reports). The technical problem may relate to training the visual ML model using an unlabeled training dataset where images are not assigned labels, and/or of training the NLP ML model using a mostly unlabeled training dataset where text based reports are not assigned labels, and where a small portion of the text based reports are weakly labeled. In standard approaches, labels improve the accuracy of the ML model(s), in particular when the size of the labelled training dataset is large, for example, supervised training of neural networks using many labelled medical images improves the accuracy of the trained neural network. However, a large training dataset of labelled medical images and/or text based reports is difficult to obtain. The labels are generally manually provided by a trained radiologist, which has limited time to accurately generate such labels. Approaches that are based on automatically extracting labels from other data, and labelling the medical images using the automatically extracted labels are prone to error. Errors in extracting accurate labels may arise, for example, from inaccuracy of the underlying data (e.g., radiology report corresponding to a medical image is incorrect, and/or data therein is irrelevant to the desired labels) and/or inaccuracy of the automated label extraction process. The automated process may extract inaccurate labels.

At least some implementations of the systems, methods, apparatus, and/or code instructions described herein improve the technical field of training an ML model. In at least some implementations, the improvement is in the ability to train a highly accurate ML model (e.g., neural network, or other implementation of a statistical classifier), such as an NLP ML model that identifies NLP categories indicative of clinical findings in text based reports of medical images (e.g., identifies that a text based report of a head CT scan describes the presence of an intracranial hemorrhage in the head CT scan), and/or a visual ML model that identifies visual findings in medical images (e.g., identifies an intracranial hemorrhage in a head CT scan). Using traditional approaches, NLP ML models are trained using a supervised approach on a training dataset of text based reports, which may be weakly labelled with the NLP categories depicted therein that serve as ground truth (i.e., the weak label is for the text report as a whole, without identifying which portion of the text report actually defines the label). Visual ML models are trained using a supervised approach on a training dataset of medical images, which are labelled with the visual findings depicted therein that serve as ground truth.

At least some implementations of the systems, methods, apparatus, and/or code instructions described herein address the above mentioned technical problem and/or improve the field of training ML models using a training dataset of records, where each record includes a pair of an image and corresponding text based report (e.g., radiology report manually generated by a radiologist reviewing the image), where none or few of the text based reports are initially labelled with a ground truth label (i.e., weak supervision) and none of the images are labeled. The training process may be entirely automated requiring no manual labelling. A small number of text based reports may be automatically weakly labelled using a simple set of rules that may inaccurately generate labels. The errors in the initial weak labelling may be fixed during the concurrent training. Alternatively, the small number of weak labels for the text based reports may be performed manually, and may be inaccurate, for example, performed by a non-expert. The initial labelling is not necessarily accurate and/or complete. For example, the initial labelling and/or initial size of labelled samples would not be accurate enough and/or large enough to generate a training dataset for training an ML component (e.g., neural network) to a target accuracy level that would be using a standard approach. However, such inaccurately labelled and/or incompletely labelled training dataset, using the concurrent training approach described herein, may train the ML component to reach the target accuracy level.

The NLP ML model and visual ML model are concurrently trained using the training dataset, where the small number of weak labels serve as an initial seed. During the concurrent training the output of the NLP ML model is used to supervise train the visual ML model, and the output of the visual ML mode is used to supervise train the NLP ML model. The concurrent training generates a trained NLP ML model and a trained visual ML model, which may be used independently. The generated NLP model is predicted to perform better (e.g., high accuracy) than a naïve NLP baseline which is trained only on weakly labelled text based reports. The NLP model may be used to assign computed labels to new text based reports. This may be beneficial as the mistakes of the NLP and visual model don't necessarily correlate (e.g., an NLP model mistake could stem from a radiologist mistake and NLP model is not affected by changes in the image capturing hardware device that captures medical images, etc.). The generated visual model is predicted to perform better (e.g., high accuracy) than a naïve visual baseline which is trained only on weakly labelled images. The visual model may be used to assign computed labels to new images.

At least some implementations of the systems, methods, apparatus, and/or code instructions described herein operate differently than other approaches. In at least some embodiments, the NLP ML model component and the visual ML model component are concurrently trained on a training dataset of pairs of images and corresponding text based reports, optionally using a combined loss function used by both ML models and another loss function used only by the NLP ML model. The outcome of the NLP ML model component (i.e., NLP classification for the report) is used as ground truth for training the visual ML model component, while concurrently the outcome of the visual ML model component (i.e., indication of visual feature depicted in the image) is used as ground truth for training the NLP ML model component. The concurrent training improves accuracy of the trained visual ML model component and/or the trained NLP model component. The accuracy may be improved, based on the expectation that the image and corresponding radiology depict/include the same visual feature, which is the same expected outcome of both the visual ML model component and the NLP model component. Correlation (i.e., different outcomes) between the visual ML model component and the NLP model component may indicate accurate predictive abilities of the respective components. For example, for a CT image depicting an intracranial hemorrhage, and a for the corresponding radiology report in which the radiologists identified the intracranial hemorrhage, both the visual ML model component and the NLP model component are predicted to output an indication of intracranial hemorrhage.

The concurrent training approach described herein is different than other approaches. Other approaches use pairs of text and images together, throughout the training approach, treating the pair of text and image as a single data structure. For example, some approaches are based on encoding images together with text to create a combined encoding. The combined encoding may be decoded. In another example, joint text-image embeddings are obtained. A network is trained to minimize differences between pairs of text and images, such as using a k-nearest neighbor approach. The concurrent training approach, where an NLP ML model and a visual ML model are concurrently trained, each using respective images or text, generates both a trained NLP ML model and a trained visual ML model, that can each be used individually without needing the full pair of images and text. In other words, the generated visual ML model may be used to classify medical images, by feeding the medical images into the visual ML model without necessarily requiring the text based report.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
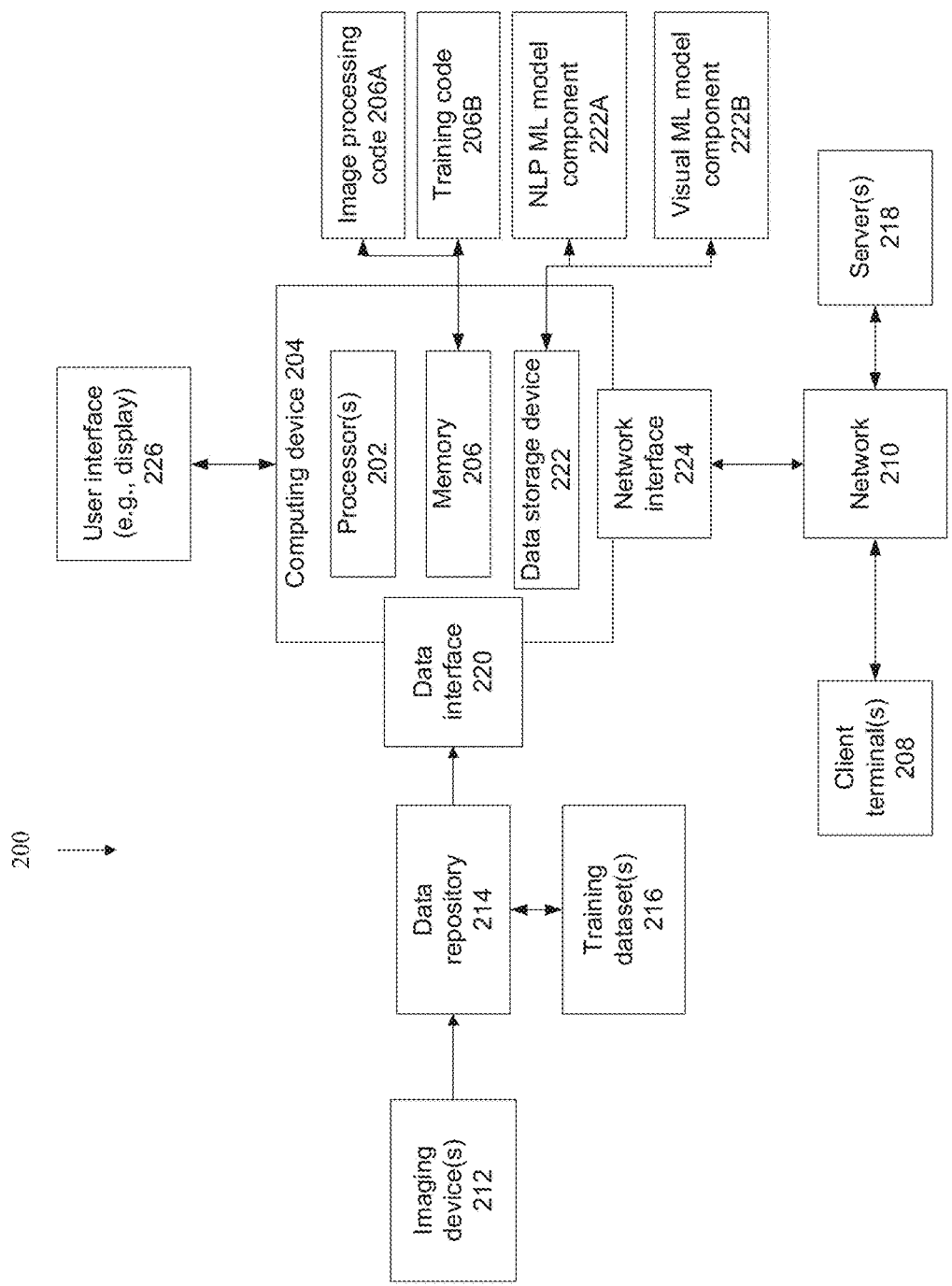
FIG. 2 is a block diagram of components of a system for concurrent training of a visual machine learning (ML) model component and a natural language processing (NLP) ML model component and/or using the trained visual ML model and/or the NLP ML model, in accordance with some embodiments of the present invention.
Figure 3:
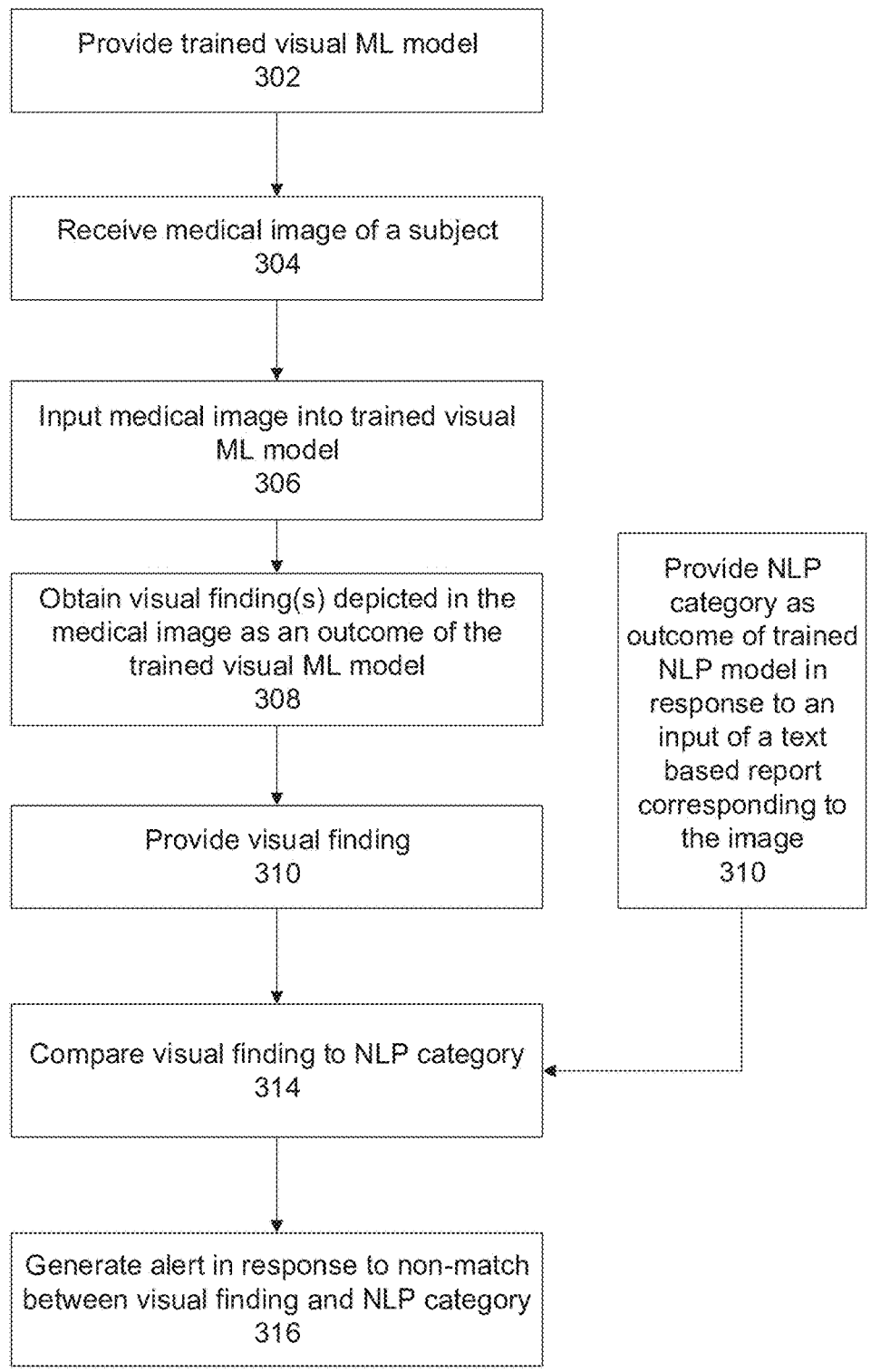
FIG. 3 is a flowchart of a method of identification of at least one visual finding in a medical image using a visual ML model concurrently trained with a NLP ML model, in accordance with some embodiments of the present invention.
Figure 4:
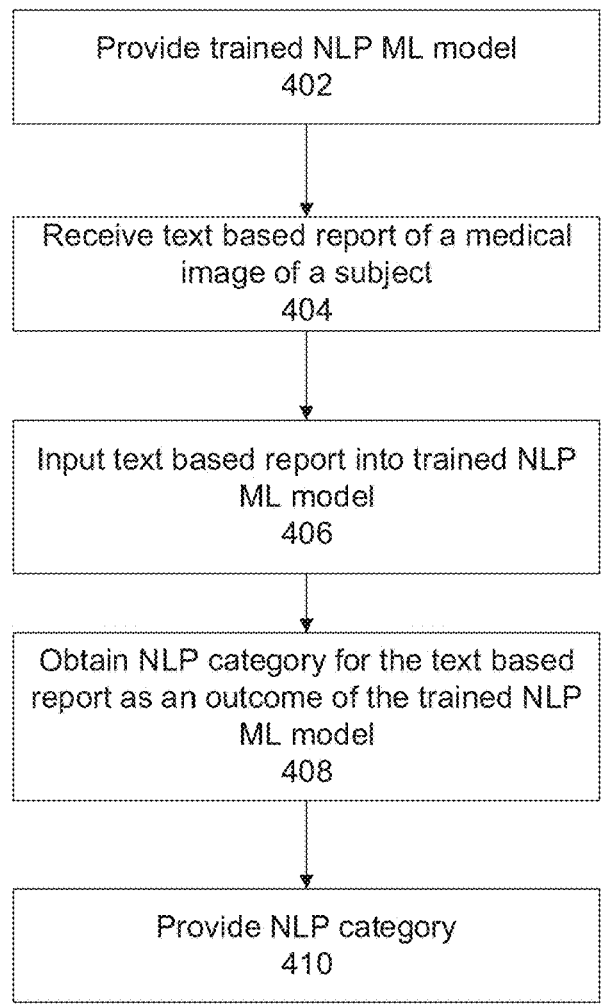
FIG. 4 is a flowchart of a method of identification of at least one NLP category in a text based report of a medical image using an NLP ML model concurrently trained with a visual ML model, in accordance with some embodiments of the present invention.

Reference is now made to FIG. 1, which is a flowchart of a method for concurrent training of a visual machine learning (ML) model component and a natural language processing (NLP) ML model component, in accordance with some embodiments of the present invention. Reference is also made to FIG. 2, which is a block diagram of components of a system 200 for concurrent training of a visual machine learning (ML) model component and a natural language processing (NLP) ML model component and/or using the trained visual ML model and/or the NLP ML model, in accordance with some embodiments of the present invention. Reference is also made to FIG. 3, which is a flowchart of a method of identification of at least one visual finding in a medical image using a visual ML model concurrently trained with a NLP ML model, in accordance with some embodiments of the present invention. Reference is also made to FIG. 4, which is a flowchart of a method of identification of at least one NLP category in a text based report of a medical image using an NLP ML model concurrently trained with a visual ML model, in accordance with some embodiments of the present invention.

System 200 may implement the acts of the method described with reference to FIG. 1 and/or FIGS. 3-4, optionally by a hardware processor(s) 202 of a computing device 204 executing code instructions stored in a memory 206.

Computing device 204 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a radiology workstation and/or other devices for presenting indications of the identified visual findings and/or other computer added detections to the radiologist.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application, and/or providing functions using a remote access session to the client terminals 208, such as through a web browser.

Different architectures based on system 200 may be implemented. In one example, computing device 204 provides centralized services. Training of the visual and/or NLP ML model components is performed concurrently, as described herein. Images and/or radiology reports may be provided to computing device 204 for centralized evaluation by the trained visual and/or NLP models. Images and/or radiology reports may be provided to computing device 204, for example, via an API, a local application, and/or transmitted using a suitable transmission protocol. In another example, computing device 204 provides centralized concurrent training of the visual and/or NLP ML model components, using different training datasets provided by different client terminals 208 and/or servers 218. For example, training datasets originating from different hospitals.

Respective generated visual and/or NLP ML models may be provided to the corresponding hospitals for local use. For example, each hospital uses the visual ML model created from their own training dataset for evaluation of new images captured at the respective hospital.

Imaging device 212 provides images included in training dataset(s) 216. Image device 212 may include a 2D, 3D, and/or 4D imaging device. Imaging devices 212 may be implemented as, for example, an x-ray machine, a magnetic resonance imaging (MRI) device, a computer tomography (CT) machine, and/or an ultrasound machine. Text based reports generated from the images (e.g., radiology reports created by a radiologist that reads the images) are included within training dataset(s) 216. Training dataset(s) 216 may be stored in a data repository 214, for example, a storage server, a computing cloud, virtual memory, and a hard disk.

Training dataset(s) 216 are used to concurrently train the NLP and visual ML models, as described herein. It is noted that training dataset(s) 216 may be stored by a server 218, accessibly by computing device 204 over network 210, for example, a publicly available training dataset, and/or a customized training dataset (e.g., created by a hospital for obtaining a customized NLP and/or visual ML model), as described herein.

Computing device 204 may receive the training dataset(s) 216 from imaging device 212 and/or data repository 214 using one or more data interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 206 may store image processing code 206A that implement one or more acts and/or features of the method described with reference to FIG. 3, and/or training code 206B that execute one or more acts of the method described with reference to FIG. 1.

Computing device 204 may include a data storage device 222 for storing data, for example, a trained NLP model 222A and/or a trained visual ML model 222B, and/or training dataset(s) 216. Data storage device 222 may be implemented as, for example, a memory, a local hard-drive, a removable storage device, an optical disk, a storage device, and/or as a remote server and/or computing cloud (e.g., accessed over network 210). It is noted that trained NLP model 222A and/or trained visual ML model 222B, and/or training dataset(s) 216 may be stored in data storage device 222, with executing portions loaded into memory 206 for execution by processor(s) 202.

Computing device 204 may include a network interface 224 for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to obtain and/or provide training dataset(s) 216, an updated version of image processing code 206A, training code 206B, and/or the trained ML model 222A-B.

It is noted that data interface 220 and network interface 224 may exist as two independent interfaces (e.g., two network ports), as two virtual interfaces on a common physical interface (e.g., virtual networks on a common network port), and/or integrated into a single interface (e.g., network interface). Computing device 204 may communicate using network 210 (or another communication channel, such as through a direct link (e.g., cable, wireless) and/or indirect link (e.g., via an intermediary computing device such as a server, and/or via a storage device) with one or more of:

Client terminal(s) 208, for example, when computing device 204 acts as a server providing image analysis services (e.g., SaaS) to remote radiology terminals, for analyzing remotely obtained anatomical images using the trained visual ML model component 222B, which may be concurrently trained by computing device 204.

Server 218, for example, implemented in association with a PACS, which may store training dataset(s) 216.

Imaging device 212 and/or data repository 214 that stores images acquired by imaging device 212. The acquired images may be evaluated by trained visual ML model 222B.

Computing device 204 and/or client terminal(s) 208 and/or server(s) 218 include and/or are in communication with a user interface(s) 226 that includes a mechanism designed for a user to enter data (e.g., patient data) and/or view the indications of identified visual findings. Exemplary user interfaces 226 include, for example, one or more of, a touchscreen, a display, a keyboard, a mouse, and voice activated software using speakers and microphone.

Referring now back to FIG. 1, at 102, a training dataset is provided and/or created. The training dataset includes, a medical image and a corresponding text based report for the medical image, for each of multiple sample individuals.

Each pair of medical image and corresponding text based report for the medical image may be referred to herein as a record.

The medical image may be an anatomical image. The medical image may be a 2D and/or 3D medical image. The medical image may be a single medical image (e.g., chest x-ray, head CT scan), and/or part of a sequence of medical images (e.g., slices of a CT scan, frames of a video such as captured by a colonoscope during a colonoscopy procedure). Examples of medical images include: chest x-ray used to evaluate findings such a pneumonia, and head CT scan used to evaluate for intracranial bleeding.

The corresponding text based report is created for the medical image. The text based report describes one or more visual findings depicted in the corresponding image using text, for example, "suspected pneumonia", and "signs of intracranial bleeding seen".

The text based report may be manually entered by a user, such as the radiologist or other physician (e.g., ER attendant) reading the medical image. The text based report may be created by a manual and/or automatic transcription of an audio recording of the user assessing the image.

At 104, at least a subset of the text based reports of the training dataset are labelled (also referred to herein as initially labelled). The other non-labeled text based reports remain unlabeled.

The initial weak labeling may serve as an initial seed for the iterative concurrent training. During the iterative concurrent training, errors in the initial weak labelling may be automatically corrected.

The label represents an initial ground truth label. The label may be a binary label indicative of presence or absence of the respective one or more NLP categories in respective target based reports. For example, for a report of a head CT being evaluated for an intracranial hemorrhage (ICH), the label may be a YES/NO label indicating whether the respective report indicates that the head CT image depicts ICH.

The subset may include, for example, less than about 1%, or 5%, or 10%, or 15%, or 20%, or 25% of the total reports, or for example, about 1-25%, or 5-20%, or 3-15%, or other ranges. The subset may include, for example, less than about 1, or 5, or 10, or 15, or 20, or 25 images, or for example, about 1-25, or 5-20, or 3-15 images. The other part of the subset remains non-labelled. As described herein, a small number of images are initially labeled manually and/or automatically, rather than requiring a fully labelled training dataset as in standard approaches, which reduces resources required for the labelling.

The labelling may be a weak labelling, for the respective text based report as a whole, without necessarily indicating which text portion in the report the labelling is associated with.

The initial labelling is not necessarily accurate and/or complete. For example, the initial labelling and/or initial size of labelled samples would not be accurate enough and/or large enough to generate a training dataset for training an ML component (e.g., neural network) to a target accuracy level that would be using a standard approach. However, such inaccurately labelled and/or incompletely labelled training dataset, using the concurrent training approach described herein, may train the ML component to reach the target accuracy level.

Errors in the initial labels are corrected during the concurrent training, based on the analysis of the corresponding image, as described herein. As such, the initial labeling may be performed manually (e.g., by simply trained users, such as medical students), and/or may be performed automatically, for example, by code based on a simple set of rules which is not necessarily accurate. For example, all text based reports that include the word "bleed" are automatically labelled as positive for ICH.

The labelling of the subset of the text based reports of the training dataset (e.g., with the weak label) is performed prior to the concurrent training described with reference to 106. The concurrently training is performed using the training dataset with weak labels of the subsample of the text based reports.

At 106, an NLP ML model component is provided. The NLP ML model component is designed to receive an input of a target text based report, and generate as an outcome, an indication of one of more NLP categories depicted in the target text based report, for example, whether ICH is depicted in the text based report or not.

The NLP ML model component may be implemented as a neural network, optionally a binary classifier.

Optionally, the NLP ML model is in an initial state, having undergone no training on the training dataset. For example, initial weights of neurons of the neural network implementation of the NLP ML model are set to random values.

At 108, a visual ML model component is provided. The visual ML model component is designed to receive an input of a target image, and generate as an outcome, an indication of one or more visual finding depicted in the target image, for example, whether ICH is depicted in the target image.

The visual ML model component may be implemented as a neural network, optionally a binary classifier.

Optionally, the visual ML model is in an initial state, having undergone no training on the training dataset. For example, initial weights of neurons of the neural network implementation of the visual ML model are set to random values.

At 110, the NLP ML model component and the visual ML model component are concurrently trained, optionally iteratively concurrently trained, using the training dataset, which may include the subset of labelled text based reports. The NLP ML model component and the visual ML model component are concurrently trained using records of the training dataset, where each record includes a medical image and corresponding text based report for the medical image.

The outcome of the NLP ML model (in response to an input of text based reports for which the corresponding images are inputted into the visual ML model) is used to supervise the training of the visual ML model (which receives the image as input, where the images correspond to the text based reports inputted into the NLP ML model to generate the outcome) by providing the labels for the images, while concurrently, the outcome of the visual ML model (in response to an input of the images for which the corresponding text based reports are inputted into the NLP ML model) is used to supervise the training of the NLP ML model (which receives the text reports as input, where the text reports correspond to the images inputted into the visual ML model to generate the respective outcome) by providing the labels for the text based reports.

The concurrent training is done by simultaneously training the NLP ML model using an input of the text based reports of the training dataset (corresponding to image(s) serving as input into the visual ML model), and using a ground truth defined as the visual finding outcome of the visual ML model in response to an input of the image(s) corresponding to the text based report(s) of the training dataset serving as input into the NLP ML model. Simultaneously, the visual ML model is trained using an input of the image(s) of the training dataset (which correspond to the text based reports used as input into the NLP ML model) and a ground truth defined as the one or more NLP categories outcome of the NLP ML model in response to an input of the text based reports of the training dataset (which correspond to the images of the training dataset used as input into the visual ML model)

Optionally, the NLP category outcome of the NLP ML model and the visual finding outcome of the visual ML model are from a common set and of a same format. The NLP category and the visual finding may be defined as the same category/outcome, having the same possible value. For example, for a head CT scan, and associated text based report for the head CT scan prepared by a radiologist, both the visual finding outcome and the NLP category outcome may be the same, for example, whether ICH is depicted. I.e., the NLP category outcome of the NLP ML model is an indication of whether the text based report indicates that ICH is present or not in the associated head CT scan, and the visual finding outcome of the visual ML model is an indication of whether ICH is present or not in the head CT scan.

Optionally, a target text report is inputted into an NLP processing path that includes the NLP ML model component that generates the NLP category, and a target image corresponding to the target text report is simultaneously inputted in a visual processing path that includes the visual ML model component that generates the visual finding. The NLP processing path and the visual processing path are concurrently executed during the concurrent training.

Optionally, the NLP category outcome of the NLP ML model and/or the visual finding outcome of the visual ML model are a binary classification indicative of positive or negative finding found in the image and corresponding text based report.

The NLP category outcome of the NLP ML model component is an indication of a visual finding depicted in the image (inputted into the visual ML model) corresponding to the text based report inputted into the NLP ML model component. The visual finding outcome of the visual ML model component is an indication of the visual finding depicted in the image (inputted into the visual ML model) corresponding to the text based report inputted into the NLP ML model component.

Optionally, the concurrent training is performed using two loss functions.

A first loss function is an NLP loss function used for training the NLP ML model component (concurrently with the visual ML model component). The NLP loss function is computed for the training of the NLP ML model (which occurs concurrently with the visual ML model component) and excludes data obtained from the concurrent training of the visual ML model component, i.e., the NLP loss function is only for the NLP ML model and is not used for training of the visual ML model, is not affected by the concurrently trained visual ML model component, and/or does not directly impact the visual ML model component. Optionally, the NLP ML model is implemented as a binary classifier and the NLP loss function is implemented as a standard binary cross entropy loss. The first loss function may penalize the NLP ML model for errors in the initial labelling, which may correct such errors in the initial labelling. The first loss function may prevent or reduce risk of the ML models collapsing into a degenerate solution (e.g., all images predicted as being negative for all findings).

A second loss function is a combined visual and NLP consensus loss function, used for the concurrent training of the NLP ML model component and the visual ML model component. Each one of the NLP ML model and the visual ML model components uses the combined visual and NLP consensus loss function (i.e., the second loss function).

The combined visual and NLP consensus loss function is impacted by the training of both the visual ML model and the NLP ML model, and impacts the training of both the visual ML model and the NLP ML model. The combined visual and NLP consensus loss function includes a cross model consensus loss function that encourages high consensus between the NLP ML model and the visual ML model.

The magnitude of the losses of the first and/or second loss functions may be a hyperparameter that is tuned during training.

The initial labelling of the text based reports (e.g., as described with reference to feature 104) may be used as supervision training for the NLP ML model, which in turn pushes the second cross-modal consensus loss function into the right direction.

It is noted that the NLP ML model and the visual ML model share the second loss function, i.e., the same second loss function is used to train both the NLP ML model and the visual ML model. However, the NLP ML model and the visual ML model do not necessarily share neuron weights.

Examples of possible combined loss functions:
Combined cross entropy:

$$L_{consensus}(\hat{y}_{vision}, \hat{y}_{NLP}) = L_{cross\text{-}entropy}(\hat{y}_{vision}, \hat{y}_{NLP}) + L_{cross\ entropy}(\hat{y}_{NLP}, \hat{y}_{vision})$$

Where:

$$L_{cross\text{-}entropy}(\hat{y}_a, \hat{y}_b) = -\hat{y}_a \log(\hat{y}_b) - (1-\hat{y}_a)\log(1-\hat{y}_b)$$

KL divergence:

$$L_{consensus}(\hat{y}_{vision}, \hat{y}_{NLP}) = D_{KL}(\hat{y}_{vision} \| \hat{y}_{NLP}) + D_{KL}(\hat{y}_{NLP} \| \hat{y}_{vision})$$

Where:

$$D_{KL}(\hat{y}_a \| \hat{y}_b) = \sum_{i \in labels} \hat{y}_a^i \log\left(\frac{\hat{y}_a^i}{\hat{y}_b^i}\right)$$

At 112, the trained NLP ML model component is provided, for generating an indication of the NLP category outcome(s) for an input of a new text based report associated with a new image.

The generated NLP model is predicted to perform better (e.g., high accuracy) than a naïve NLP baseline which is trained only on weakly labelled text based reports. The NLP model may be used to assign computed labels to new text based reports. This may be beneficial as the mistakes of the NLP and visual model don't necessarily correlate (e.g., an NLP model mistake could stem from a radiologist mistake and NLP model is not affected by changes in the image capturing hardware device that captures medical images, etc.).

At 114, the trained visual ML model component is provided, for generating an indication of the visual category for an input of a new image. It is noted that the trained visual ML model and the trained NLP ML model may be used independently, and/or together.

The generated visual model is predicted to perform better (e.g., high accuracy) than a naïve visual baseline which is trained only on weakly labelled images. The visual model may be used to assign computed labels to new images.

At 116, during and/or after the concurrent training described with reference to 110, a correlation value indicative of a correlation between the NLP category outcome of the NLP ML model (in response to an input of a certain text based report corresponding to a certain image) and the visual finding outcome of the visual ML model (in response to an input of the certain image corresponding to the certain text based report inputted into the NLP ML model) is computed. The correlation value may be binary, for example, indicating whether the NLP category and the visual finding are the same, or different. The correlation value may be a numerical value, for example, between 0-1, or 0-100 or other ranges, for example indicative amount of similarity.

At 118, in response to the correlation value for the NLP category outcome of the NLP ML model and the visual finding outcome of the visual ML model, being below a threshold indicative of dis-correlation (e.g., non-correlation) and/or the correlation value equal to the binary value indicative of dis-correlation, the image (fed into the visual ML model) and corresponding text based report (simultaneously fed into the NLP ML model) may be stored, for example, in a user-training dataset. The user-training dataset represents radiology imaging cases that be difficult for interpretation, for example, cases which require additional time, and/or training. The user-training dataset may be provided, for example, for presentation on a display. For example, the images and corresponding text reports may be used to generate a presentation for training radiologists on difficult cases where the automated ML models made mistakes, and/or may be used to generate a test for testing radiologists.

Referring now back to FIG. 3, at 302, a trained visual ML model is provided. The visual ML model component generates an outcome of visual finding(s) in response to an input of a target image.

The visual ML model is a visual ML model component that is concurrently trained with an NLP ML model component on a training dataset including, for each of multiple sample individuals, a medical image and a corresponding text based report (for the medical image).

The concurrently training is performed by training the NLP ML model using an input of the text based reports of the training dataset and a ground truth defined the outcome of the visual finding(s) generated by the visual ML model in response to an input of the image(s) corresponding to the text based reports of the training dataset (which are inputted into the NLP ML model). Concurrently, the visual ML model is trained using an input of the image(s) of the training dataset and a ground truth defined as the outcome of the NLP category generated by the NLP ML model in response to the input of the text based report(s) corresponding to the image(s) of the training dataset inputted into the visual ML model.

Additional details of concurrently training of the NLP ML model and the visual ML model are described, for example, with reference to 110 of FIG. 1.

At 304, a medical image of a subject is received. For example, from the PACS server, outputted by the imaging machine, from a detachable portable memory, from a hard disk, from a remote device, and/or other locations.

At 306, the medical image is inputted into the trained visual ML model.

At 308, an indication of one or more visual finding depicted within the medical image is obtained as an outcome of the visual ML model.

At 310, the visual finding(s) are provided, for example, presented on a display, stored in a data storage device (e.g., in the medical record of the subject, in the PACS server in association with the image (e.g., as metadata), forwarded to another device and/or server, and/or forwarded to another process (e.g., application) for further processing.

At 312, one or more NLP categories are obtained as an outcome of the NLP ML model.

The outcome is generated by the NLP ML model in response to receiving an input of the text based report corresponding to the medical image inputted into the visual ML model. The NLP ML model component is concurrently trained with the visual ML model component on the training dataset, as described herein.

The NLP category is indicative of visual finding(s) depicted within the medical image (inputted into the visual ML model, which is also described in the text based report inputted into the NLP model).

At 314, the NLP category is compared to the visual finding to determine whether the NLP category matches the visual finding category. Since the text report is a text description of the visual contends depicted within the corresponding visual image, a match indicates that the NLP ML model and the visual ML model likely worked correctly, since they both found the same result in the image and text report. A non-match may indicate that there is a problem and/or error somewhere, for example, in the text report, in the outcome of the visual ML model, and/or in the outcome of the NLP ML model.

At 316, an alert may be generated in response to the NLP category outcome of the NLP ML model not matching the visual finding outcome of the visual ML model. The alert may be an indication for a user (e.g., radiologist) to examine the image and corresponding text (and/or NLP ML model and/or visual ML model) for errors. The alert may be, for example, presented on a display, stored as a pop-up message that appears when the patient record is accessed, stored as metadata associated with the image and/or report, and/or an email sent to an administrator.

Referring now back to FIG. 4, at 402, a trained NLP ML model is provided.

The NLP model is an NLP ML model component that is concurrently trained with a visual ML model component as described herein, for example, as described with reference to feature 110 of FIG. 1 and/or feature 302 of FIG. 3.

At 404, a text based report of a medical image of a subject is received, for example, from the EMR server, typed by a user, from an automated transcription service that automatically transcribes dictations, from a data storage device, and/or from another storage location.

At 406, the text based report is inputted into the NLP ML model.

At 408, an indication of one or more NLP categories indicative of visual finding(s) of the medical image described in the text based report is obtained as an outcome of the NLP ML model.

At 410, the NLP category is provided, for example, presented on a display, stored in a data storage device (e.g., in the medical record of the subject, in the PACS server in association with the image (e.g., as metadata), forwarded to another device and/or server, and/or forwarded to another process (e.g., application) for further processing.

Figure 5:
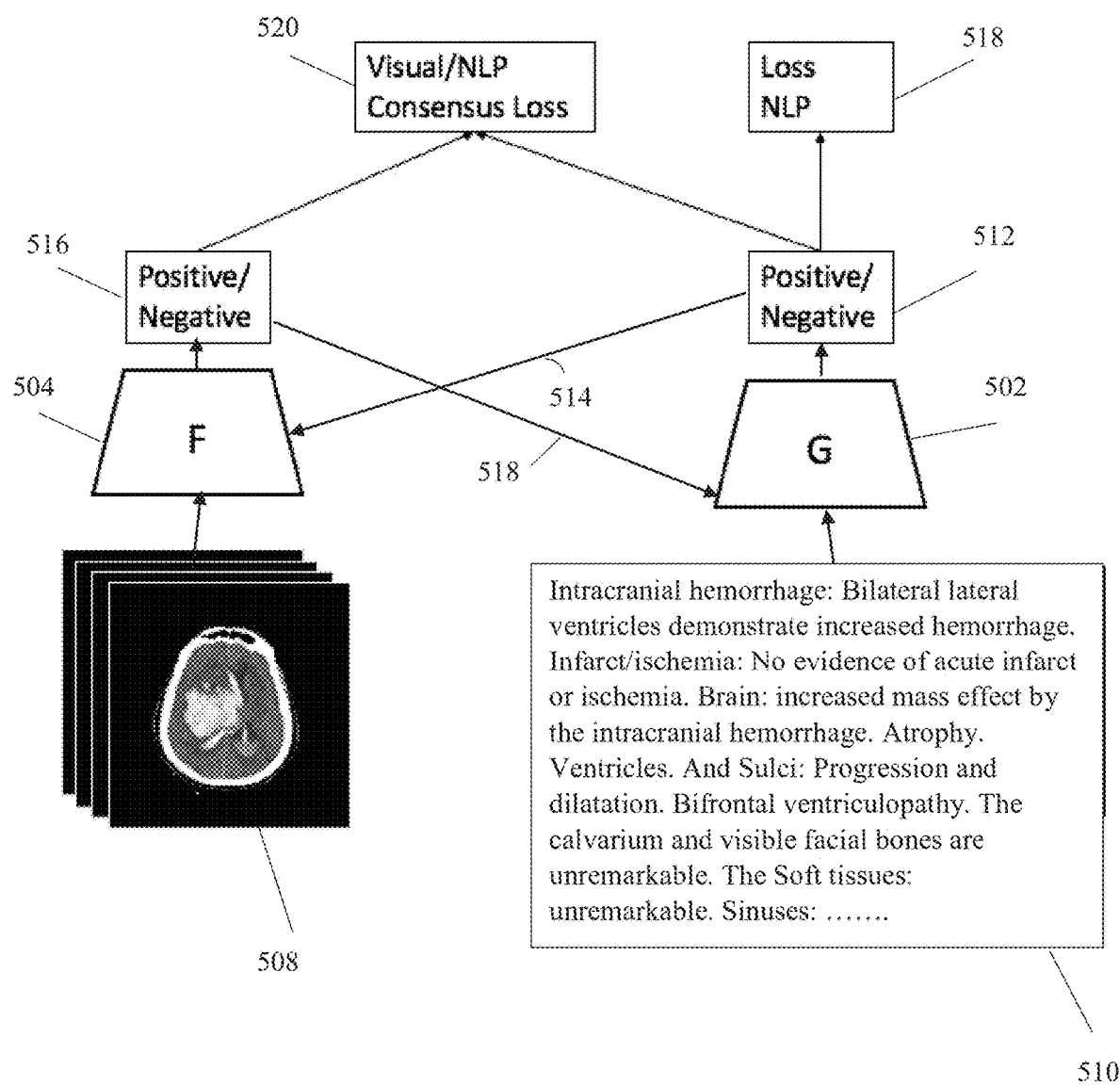
FIG. 5 is a schematic depicting concurrent training, optionally iteratively concurrently, of an NLP ML model component and a visual ML model component using a training dataset that includes records of medical images and text based reports corresponding to the medical images, in accordance with some embodiments of the present invention.

Reference is now made to FIG. 5, which is a schematic depicting concurrent training, optionally iteratively concurrently, of an NLP ML model component 502 and a visual ML model component 504 using a training dataset that includes records of medical images 508 and text based reports 510 corresponding to medical images 508, in accordance with some embodiments of the present invention. An outcome 512 of NLP ML model 502 (in response to an input of text based reports 510 for which the corresponding images 508 are inputted into visual ML model 504) is obtained, and used to supervise 514 the training of visual ML model 504 (which receives the images 508 as input, where the images 508 correspond to the text based reports 510 inputted into NLP ML model 502 to generate the outcome). Outcome 512 may be, for example, a binary value, indicating whether a certain NLP category is identified for text based report 510 by NLP ML model 502. Concurrently, an outcome 516 of visual ML model 504 (in response to an input of images 508 for which the corresponding text based reports 510 are inputted into the NLP ML model 502) is used to supervise 518 the training of the NLP ML model 502 (which receives the text reports 510 as input, where the text reports 510 correspond to the images 508 inputted into the visual ML model 504 to generate the respective outcome 516). During the concurrent training, NLP ML model 502 is trained on a first loss function 518. First loss function 518 is not used for training of visual ML model 504. During the concurrent training, both NLP ML model 502 and visual ML model 504 are trained using a second loss function 520, also referred to herein as a visual/NLP and/or combined and/or consensus loss function. NLP ML model 502 and visual ML model 504 use the same second loss function 520 during the concurrent training.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant ML models will be developed and the scope of the term ML model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method for training a visual machine learning (ML) model component and a natural language processing (NLP) ML model component, comprising:
providing a training dataset including, for each of a plurality of sample individuals, a medical image and a corresponding text based report;
providing the NLP ML model component for generating an outcome of at least one NLP category in response to an input of a target text based report;
providing the visual ML model component for generating an outcome of at least one visual finding in response to an input of a target image; and
concurrently training the NLP ML model component and the visual ML model component using the training dataset, by:
training the NLP ML model using an input of the text based reports of the training dataset and a ground truth comprising the outcome of the at least one visual finding generated by the visual ML model in response to an input of the images corresponding to the text based reports of the training dataset;
training the visual ML model using an input of the images of the training dataset and a ground truth comprising the outcome of the at least one NLP category generated by the NLP ML model in response to an input of the text based reports corresponding to the images of the training dataset;

computing a correlation value indicative of a correlation between the at least one NLP category outcome of the NLP ML model and the at least one visual finding outcome of the visual ML model for an input of an image and corresponding text based report; and in response to the correlation value being below a threshold indicative of dis-correlation between the at least one NLP category outcome of the NLP ML model and the at least one visual finding outcome of the visual ML model, storing the image and corresponding text based report in a user-training dataset; and providing the user-training dataset for presentation on a display.

2. The method of claim 1, wherein the NLP ML model is trained using a supervised approach with the input of the based reports and the ground truth outcome of the visual ML model, and concurrently the visual ML model is trained using a supervised approach with the input of the images and the ground truth outcome of the NLP ML model.

3. The method of claim 1, wherein the concurrently training is performed iteratively.

4. The method of claim 1, further comprising:
prior to the concurrently training, weakly labelling a subset of the text based reports of the training dataset with a weak label indicative of presence or absence of the at least one NLP category in respective target based reports; and wherein the concurrently training is performed using the training dataset with weak labels of the text based reports.

5. The method of claim 4, wherein weakly labelling comprises weakly labelling about 5-20% of the text based reports of the training dataset with the weak label.

6. The method of claim 4, wherein weakly labelling comprises automatically weakly labelling the subset of the text based reports using a simple set of rules.

7. The method of claim 1, wherein the at least one NLP category outcome of the NLP ML model and the at least one visual finding outcome of the visual ML model are from a common set and of a same format.

8. The method of claim 1, wherein each of the at least one NLP category outcome of the NLP ML model and the at least one visual finding outcome of the visual ML model is a binary classification indicative of positive or negative finding found in the image and corresponding text based report.

9. The method of claim 1, wherein the at least one NLP category outcome of the NLP ML model component is an indication of a visual finding depicted in an image corresponding to a text based report inputted into the NLP ML model component, and the at least one visual finding outcome of the visual ML model component is an indication of the visual finding depicted in the image corresponding to the text based report inputted into the NLP ML model component.

10. The method of claim 1, wherein concurrently training comprises concurrently training the NLP ML model component and the visual ML model component using a combined visual and NLP consensus loss function.

11. The method of claim 1, wherein the combined visual and NLP consensus loss function comprises a cross model consensus loss function that encourages high consensus between the NLP ML model and the visual ML model.

12. The method of claim 10, wherein concurrently training further comprises training the NLP ML model component using an NLP loss function that is computed for the training of the NLP ML model and excludes data obtained from the training of the visual ML model component.

13. The method of claim 12, wherein the NLP ML model comprises a binary classifier and the NLP loss function comprises a standard binary cross entropy loss.

14. The method of claim 12, wherein the NLP loss function penalizes the NLP ML model for errors made during an initial inaccurate labeling of a subset of text based reports of the training dataset made prior to the concurrently training.

15. The method of claim 1, wherein the visual ML model component is implemented as a neural network.

16. The method of claim 1, wherein the NLP ML model component is implemented as a neural network.

17. The method of claim 1, wherein a target text report is inputted into an NLP processing path comprising the NLP ML model component that generates the NLP category, and a target image corresponding to the target text report is inputted in a visual processing path comprising the visual ML model component that generates the at least one visual finding, wherein the NLP processing path and the visual processing path are concurrently executed during the concurrent training.

* * * * *